United States Patent
Pradhan et al.

(10) Patent No.: US 10,520,381 B2
(45) Date of Patent: Dec. 31, 2019

(54) PHOTONIC PRESSURE SENSOR DEVICE AND METHODS OF USE THEREOF

(71) Applicant: Micatu Inc., Horseheads, NY (US)

(72) Inventors: Atul Pradhan, Pittsford, NY (US); Scott Stelick, Slaterville Springs, NY (US)

(73) Assignee: Micatu Inc., Horseheads, NY (US)

( * ) Notice: Subject to any disclaimer, the term of this patent is extended or adjusted under 35 U.S.C. 154(b) by 0 days.

(21) Appl. No.: 15/972,730

(22) Filed: May 7, 2018

(65) Prior Publication Data

US 2018/0321101 A1 Nov. 8, 2018

Related U.S. Application Data

(60) Provisional application No. 62/502,947, filed on May 8, 2017.

(51) Int. Cl.
*G01J 1/56* (2006.01)
*G01L 9/00* (2006.01)
(Continued)

(52) U.S. Cl.
CPC .............. *G01L 9/0076* (2013.01); *G01J 1/56* (2013.01); *G01N 21/4133* (2013.01);
(Continued)

(58) Field of Classification Search
CPC ........ G02B 26/001; G02B 1/002; G02B 1/02; G02B 26/0841; G02B 1/041; G02B 26/004; G02B 26/005; G02B 26/0833; G02B 3/12; G02B 3/14; G02B 6/12007; G02B 6/122; G02B 6/29358; G02B 6/3552;
(Continued)

(56) References Cited

U.S. PATENT DOCUMENTS

2004/0202400 A1 * 10/2004 Kochergin ......... G01D 5/35316
385/12
2007/0084992 A1 * 4/2007 Hammig ............... F25B 23/003
250/251

(Continued)

OTHER PUBLICATIONS

Bom et al., Principles of Optics, 7th Edition, Cambridge University Press (1999).

(Continued)

Primary Examiner — Michael P Stafira
(74) Attorney, Agent, or Firm — Pepper Hamilton LLP

(57) ABSTRACT

A photonic pressure sensor device includes a cantilever pivotally attached to a fixed mount. The cantilever has an electromagnetic reactive material located thereon that is configured to cause a movement of the cantilever based on a photonic pressure exerted on the electromagnetic reactive material from an electromagnetic radiation source incident on the material. An etalon is coupled to the cantilever such that a position of the etalon changes based on the movement of the cantilever. A light source is optically coupled to the etalon to provide a light beam to the etalon. The change in the position of the etalon causes interference of the light within the etalon resulting in an interference light beam. A light detector is positioned to receive the interference light beam from the etalon and configured to measure an intensity value for the interference light beam.

24 Claims, 5 Drawing Sheets

(51) Int. Cl.
*G02B 6/122* (2006.01)
*G01N 21/41* (2006.01)
*G01T 1/16* (2006.01)
*G01N 23/00* (2006.01)
*G02B 6/32* (2006.01)
*G02B 6/26* (2006.01)

(52) U.S. Cl.
CPC .............. *G01N 23/00* (2013.01); *G01T 1/16* (2013.01); *G02B 6/1225* (2013.01); *G02B 6/262* (2013.01); *G02B 6/32* (2013.01)

(58) Field of Classification Search
CPC ........ G02B 6/356; G02B 6/3594; G02B 6/42; G02B 6/4202; G02B 6/4206; G02B 7/003; G02B 2006/12038; G02B 2006/12061; G02B 21/02; G02B 21/06; G02B 21/26; G02B 21/34; G02B 21/361; G02B 21/365; G02B 27/56; G02B 6/02209; G02B 6/1225; G02B 6/26; G02B 6/283; G02B 6/29322; G02B 6/29395; G02B 6/3504; G02B 6/3548; G02B 6/3568; G02B 6/3596; G02B 1/118; G02B 1/12; G02B 1/14; G02B 2006/12097; G02B 2006/12104; G02B 2006/12109; G02B 2006/12126; G02B 2006/12138; G02B 2006/12159; G02B 2006/12164; G02B 2027/0125; G02B 207/0134; G02B 2027/0154; G02B 2027/0178; G02B 21/0004; G02B 21/0028; G02B 21/0064; G02B 21/0068; G02B 21/008; G02B 26/007; G02B 26/02; G02B 26/08; G02B 26/0808; G02B 27/0006; G02B 27/0081; G02B 27/0172; G02B 27/0176; G02B 27/62; G02B 5/201; G02B 5/281; G02B 6/0076; G02B 6/13; G02B 6/255; G02B 6/2551; G02B 6/2552; G02B 6/262; G02B 6/266; G02B 6/29317; G02B 6/29319; G02B 6/29338; G02B 6/3512; G02B 6/3536; G02B 6/357; G02B 6/3578; G02B 6/3584; G02B 6/3592; G02B 6/3608; G02B 6/3846; G02B 6/4215; G02B 6/43; G02B 7/004; G02B 7/005; G02B 7/023; G01N 2021/3595; G01N 21/39; G01N 2201/06113; G01N 15/14; G01N 15/1434; G01N 15/1436; G01N 15/147; G01N 15/1484; G01N 2015/0065; G01N 2015/1454; G01N 2015/149; G01N 2015/1497; G01N 21/3577; G01N 21/45; G01N 21/532; G01N 2201/12; G01N 2291/0256; G01N 29/036; G01N 33/487; G01N 1/10; G01N 2021/399; G01N 2021/757; G01N 21/17; G01N 21/75; G01N 21/1702; G01N 21/553; G01N 21/64; G01N 21/7703; G01N 1/2273; G01N 2001/022; G01N 2021/1704; G01N 2021/1734; G01N 2021/1795; G01N 2021/3513; G01N 2021/394; G01N 21/25; G01N 21/255; G01N 21/3504; G01N 21/4133; G01N 21/648; G01N 21/7746; G01N 2201/0221; G01N 2201/068; G01N 2291/02836; G01N 2291/02872; G01N 2291/0427; G01N 29/0681; G01N 29/2406; G01N 29/2418; G01N 29/2437; G01B 9/02004; G01B 2290/25; G01B 9/02051; G01B 21/042; G01B 5/008; G01B 9/02044; G01B 11/272; G01B 2290/15; G01B 2290/60; G01B 2290/70; G01B 9/02002; G01B 9/02007; G01B 9/02014; G01B 9/02041; G01B 9/02049; G01B 9/02065; G01B 9/0209; G01B 9/02091; G01J 1/4257; G01J 3/02; G01J 3/0256; G01J 3/0289; G01J 1/56; G01J 3/0202; G01J 3/0229; G01J 3/0286; G01J 3/1256; G01J 3/26; G01J 3/42; G01J 3/4338; G01J 3/4532
See application file for complete search history.

(56) References Cited

U.S. PATENT DOCUMENTS

2010/0139406 A1* 6/2010 Stievater .............. G01N 29/036
 73/655
2012/0096956 A1* 4/2012 Sabarinathan ........ G01L 9/0076
 73/862.541
2014/0307253 A1 10/2014 Lehman et al.

OTHER PUBLICATIONS

Cromer et al., "Absolute High-Power Laser Measurements with a Flowing Water Power Meter," presented at the 11th Conference on New Developments and Applications in Optical Radiometry, Maui, Hawaii, USA (Sep. 19-23, 2011) See also: http://www.nist.gov/pml/div686/laser_power_meter.cfm.

Han et al., "Dynamics of Transversely Vibrating Beams Using Four Engineering Theories," Journal of Sound and Vibration 225(5):935 (1999).

Kleppner et al., "An Introduction to Mechanics," Cambridge University Press (2010).

Li et al., "NIST Measurement Services: High Power Laser Calibrations at NIST," NIST Special Publication 250-77 (2008).

Mansuripur, M., "Radiation Pressure and the Linear Momentum of the Electromagnetic Field," Optics Express 12(22):5375-5401 (2004).

Pozar, T., "Oblique Reflection of a Laser Pulse from a Perfect Elastic Mirror," Optics Letters 39(1) (2014).

Schreiner, L.J., "On the Quality Assurance and Verification of Modern Radiation Therapy Treatment," J. Med. Phys. 36 (4):189-191 (2011).

Spiegel, M., "Theoretical Mechanics," Schaum Publishing, New York (1968).

Stephen, N. G., "The Second Spectrum of Timoshenko Beam Theory," Journal of Sound and Vibration 292:372-389 (2006).

Williams et al., "Use of Radiation Pressure for Measurement of High-Power Laser Emission," Optics Letters 38(20):4248-4251 (2013).

Wu et al., "Measurement of Photon Pressure," XVIII Imeko World Congress, Metrology for a Sustainable Development (2006).

* cited by examiner

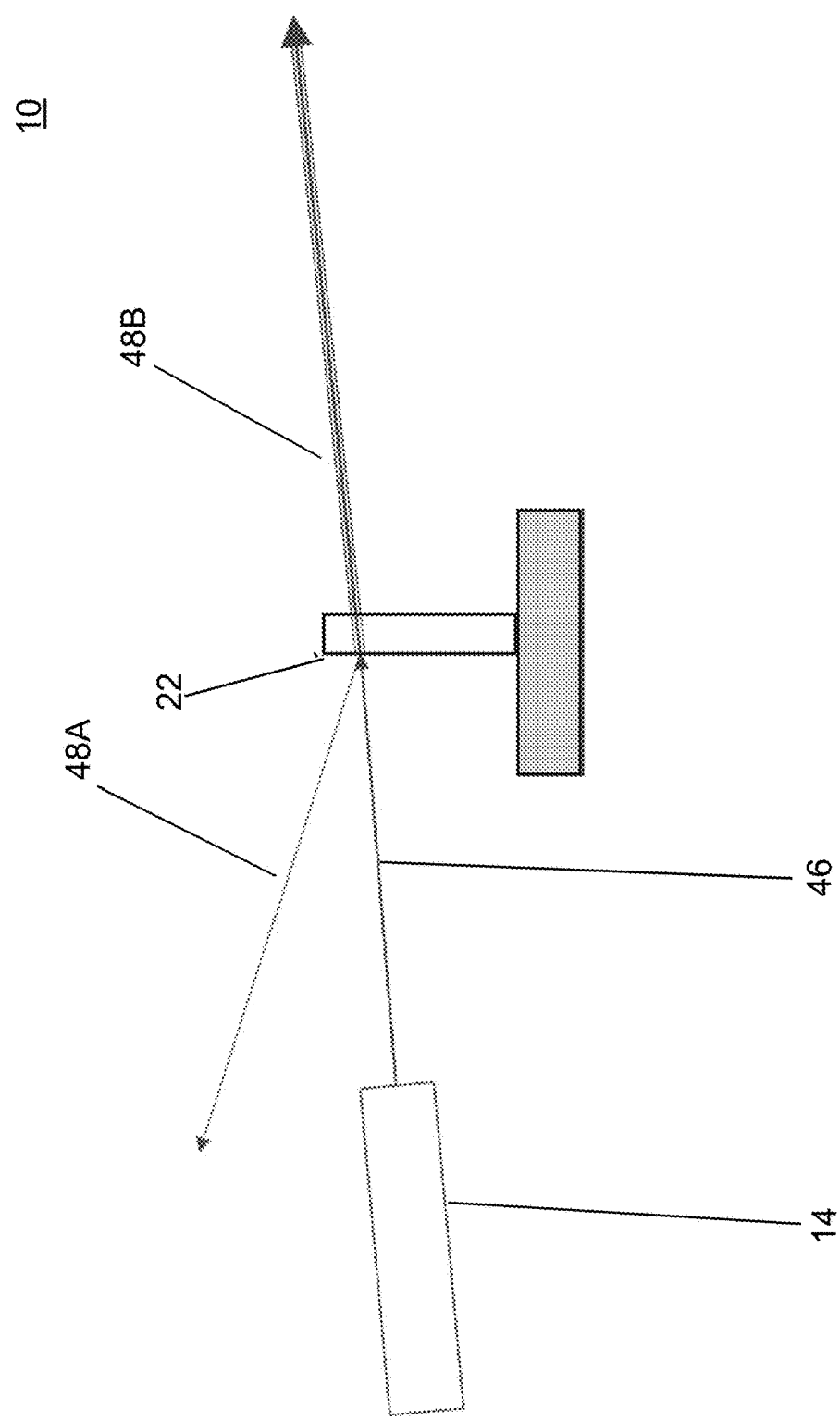

PHOTONIC PRESSURE SENSOR DEVICE AND METHODS OF USE THEREOF

This application claims the benefit of U.S. Provisional Patent Application Ser. No. 62/502,947 filed May 8, 2017, which is hereby incorporated by reference in its entirety.

FIELD OF THE INVENTION

The present technology pertains to the field of optical sensors, and the application of optical sensors to measure power from high power electromagnetic sources, including lasers and X-Rays. More specifically, the present technology relates to photonic pressure sensor devices and methods of use thereof.

BACKGROUND OF THE INVENTION

Electromagnetic radiation is radiant energy released by certain electromagnetic processes, including radio waves, microwaves, infrared (IR) light, visible light, ultraviolet (UV) light, X-rays, and gamma rays. In classical physics, electromagnetic radiation consists of waves, which are oscillations of electric and magnetic fields. Such electromagnetic waves are characterized by wavelength or frequency, which determines position on the electromagnetic spectrum. The electromagnetic spectrum runs from long large wavelength, low energy radio waves, to short wavelength, high-energy gamma rays. In quantum physics, electromagnetic radiation is described in terms of elementary particles, called photons, instead of waves.

Electromagnetic radiation forms the backbone of many modern technologies, including but not limited to, radio transmitters, microwave transmitters, X-ray equipment, and high power lasers. A key challenge in using these technologies is accurately measuring or monitoring power output. In many cases, features such as high energy levels can make it particularly difficult to accurately measure electromagnetic radiation. This difficulty in making accurate measurements has implications in many areas, such as industries where high power lasers are used in industrial processes, and in scientific research and medicine where research and treatments rely on accurate measurement of the X-ray flux.

A key challenge in the use of high-power lasers is accurately measuring and monitoring power. Current techniques used for measuring and calibrating high-power lasers involve calorimetric approaches, where incident optical energy is absorbed by a known quantity of material, and power is calculated based on the rise in temperature over time. This approach relies on a temperature response that is linear relative to the incident power absorbed. However, a key limitation is the slow response time of such methods. Another approach to determining optical power involves a flowing water method, where water is heated by the incident optical power. This method provides a more rapid response, but the size of the monitoring system must scale linearly with the power being measured. Both the calorimetric and flowing water methods require that the majority of optical power be absorbed in order to provide an accurate power reading. Another drawback of such systems is that they are not portable.

Recently, U.S. Patent Application Publication No. 2014/0307253 to Williams, et al., "Use of Radiation Pressure For Measurement of High-Power Laser Emission," Optics Letters, 38(20):4248-51 (2013), described an approach to measuring laser power via radiation pressure or force. That approach involves directing a laser beam at a direct-loading force-restoration balance having a resolution of 100 nN. The laser beam is directed incident to a mirror that is attached to the shaft of the balance, and the force of the laser beam is measured by deflection of the shaft. While such a system represents an improvement versus calorimetric approaches to measuring laser power, it suffers from drawbacks including inherent noise due to temperature drifts and ambient air movements. These drawbacks overly complicate the direct-loading force-restoration balance approach to measuring laser power.

Another area where there are challenges, similar to those encountered in measuring power from high power lasers, is in measuring X-ray flux. For example, at synchrotrons and free-electron laser facilities, the measurement of X-ray flux is necessary to align and troubleshoot optical elements. However, measuring the X-ray flux is a complicated endeavor, requiring significant time and resources that impacts research.

Likewise the accurate measurement of photon flux from an X-ray source is important for radiation therapy centers, where such measurement is key to calculating absorbed dose at a target tissue. Technologies used to measure X-ray at synchrotrons, free-electron laser facilities, and radiation therapy centers include ion chambers and diode arrays. However, these techniques have inherent limitations.

For radiation therapy, these techniques are based on dosage measurement at a specific point, which may or may not correlate with tumor volume. Such techniques have serious limitations with regard to Intensity Modulate Radiation Therapy where treatment requires dosage modulation as described in Schreiner, L. J., "On The Quality Assurance and Verification of Modern Radiation Therapy Treatment," J. Med. Phys. 36(4):189-91 (2011).

Thus, there is a need for new methods and devices for measuring and monitoring photonic pressure that can be used wherein the photonic pressure is created from electromagnetic sources, including but not limited to X-Rays, UV light, visible light, and infrared light.

The present technology is directed to overcoming these and other deficiencies in the art.

SUMMARY OF THE INVENTION

One aspect of the present technology relates to a photonic pressure sensor device. The photonic pressure sensor device includes a cantilever pivotally attached to a fixed mount. The cantilever has an electromagnetic reactive material located thereon. The electromagnetic reactive material is configured to cause a movement of the cantilever based on a photonic pressure exerted on the electromagnetic reactive material from an electromagnetic radiation source incident on the electromagnetic reactive material. An etalon is coupled to the cantilever such that a position of the etalon changes based on the movement of the cantilever. A light source is optically coupled to the etalon to provide a light beam to the etalon. The change in the position of the etalon causes interference of the light within the etalon resulting in an interference light beam. A light detector is positioned to receive the interference light beam from the etalon and configured to measure an intensity value for the interference light beam.

Another aspect of the present technology relates to a method measuring photonic pressure. The method includes providing the photonic pressure sensor device of the present invention. The photonic pressure sensor device is positioned to receive electromagnetic radiation from the electromagnetic radiation source incident on the electromagnetic reactive material. The light beam is provided to the etalon. The interference light beam is collected with the detector. The intensity value of the interference light beam is measured. The photonic pressure exerted on the electromagnetic reactive material is determined based on the measured intensity value for the interference light beam.

Yet another aspect of the present technology relates to a method of making a photonic pressure sensor device. The method includes pivotally attaching a cantilever to a fixed mount, the cantilever having an electromagnetic reactive material located thereon that is configured to cause a movement of the cantilever based on a photonic pressure exerted on the electromagnetic reactive material from an electromagnetic radiation source incident on the electromagnetic reactive material. An etalon is coupled to the cantilever such that a position of the etalon changes based on the movement of the cantilever. A light source is optically coupled to the etalon to provide a light beam to the etalon, wherein the change in the position of the etalon causes interference of the light within the etalon resulting in an interference light beam. A light detector is positioned to receive the interference light beam from the etalon. The light detector is configured to measure an intensity value for the interference light beam.

The present technology describes a photonic sensor device and methods of monitoring and measuring photonic pressure that have significant advantages over currently available technologies. The technology advantageously allows for precise and accurate measurement of photon radiation pressure by interferometrically interrogating the induced mechanical motion of a cantilevered optical element through fast sampling of a direct optical modulation signal. The devices of the present technology are advantageously portable, easy to use, and can be utilized to measure photonic pressure in a simple manner over a large dynamic range Advantages of the current invention include the simplicity of the power measuring device, and its ability to transduce photon pressure and radiation force into mechanical motion that is sensed using a modulated optical analog power signal. The device requires no electronics or electrical activity in the sensor head making it immune to electromagnetic (EM) and radio-frequency (RF) interference.

The device of the current technology provides a monolithic optical element that provides a direct conversion of photon pressure into mechanical motion, along with a cavity for interferometric detection of the mechanical displacement. These attributes provide the device with a high level of sensitivity and precision, at least an order of magnitude better than currently available laser power measurement methods, as well as a wide dynamic range. Additionally, the devices and methods of the present technology provide extremely fast response times limited only by data-acquisition, sampling, processor speeds, and high-frequency characterization of transient laser power fluctuations. The sensitivity will be maintained throughout a wide bandwidth from low to laser fluctuation frequencies, as opposed to current methods that degrade rapidly in performance at higher frequencies.

BRIEF DESCRIPTION OF THE DRAWINGS

FIG. 3 is a schematic block diagram of an exemplary etalon and cantilever mount of the present technology.

DETAILED DESCRIPTION

The present technology relates to photonic pressure sensor devices and methods of use thereof.

One aspect of the present technology relates to a photonic pressure sensor device. The photonic pressure sensor device includes a cantilever pivotally attached to a fixed mount. The cantilever has an electromagnetic reactive material located thereon. The electromagnetic reactive material is configured to cause a movement of the cantilever based on a photonic pressure exerted on the electromagnetic reactive material from an electromagnetic radiation source incident on the electromagnetic reactive material. An etalon is coupled to the cantilever such that a position of the etalon changes based on the movement of the cantilever. A light source is optically coupled to the etalon to provide a light beam to the etalon. The change in the position of the etalon causes interference of the light within the etalon resulting in an interference light beam. A light detector is positioned to receive the interference light beam from the etalon and configured to measure an intensity value for the interference light beam.

Figure 1:
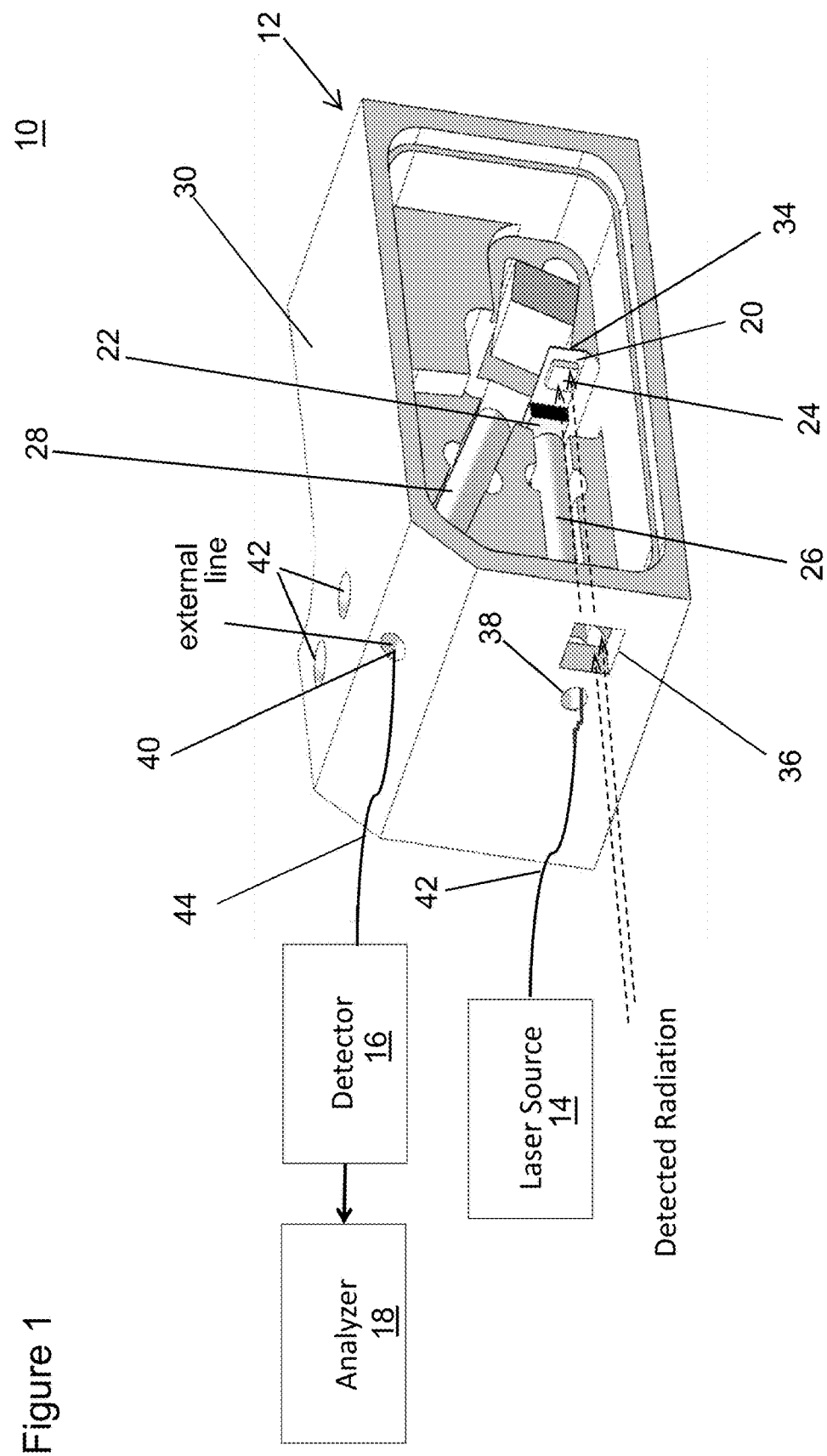
FIG. 1 is a partial side perspective cross-sectional view and a partial block diagram of a photonic pressure measurement system including a photonic pressure sensor device of the present technology.

An exemplary photonic pressure measuring system 10 is illustrated in FIG. 1. The photonic pressure measuring system 10 includes a photonic sensor device 12, a light source 14, a detector 16, and an analyzing computing device 18, although photonic pressure measuring system 10 may include other type and/or numbers of devices, components, or elements in other configurations, such as additional optical components, such as lenses or collimators, and additional electrical components, such as amplifiers and analog to digital converters. Photonic pressure measuring system 10 advantageously utilizes a monolithic optical element that provides a direct conversion of photon pressure into mechanical motion, along with a cavity for interferometric detection of the mechanical displacement. These attributes provide the device with a high level of sensitivity and precision, at least an order of magnitude better than currently available laser power measurement methods, as well as a wide dynamic range.

Figure 2:
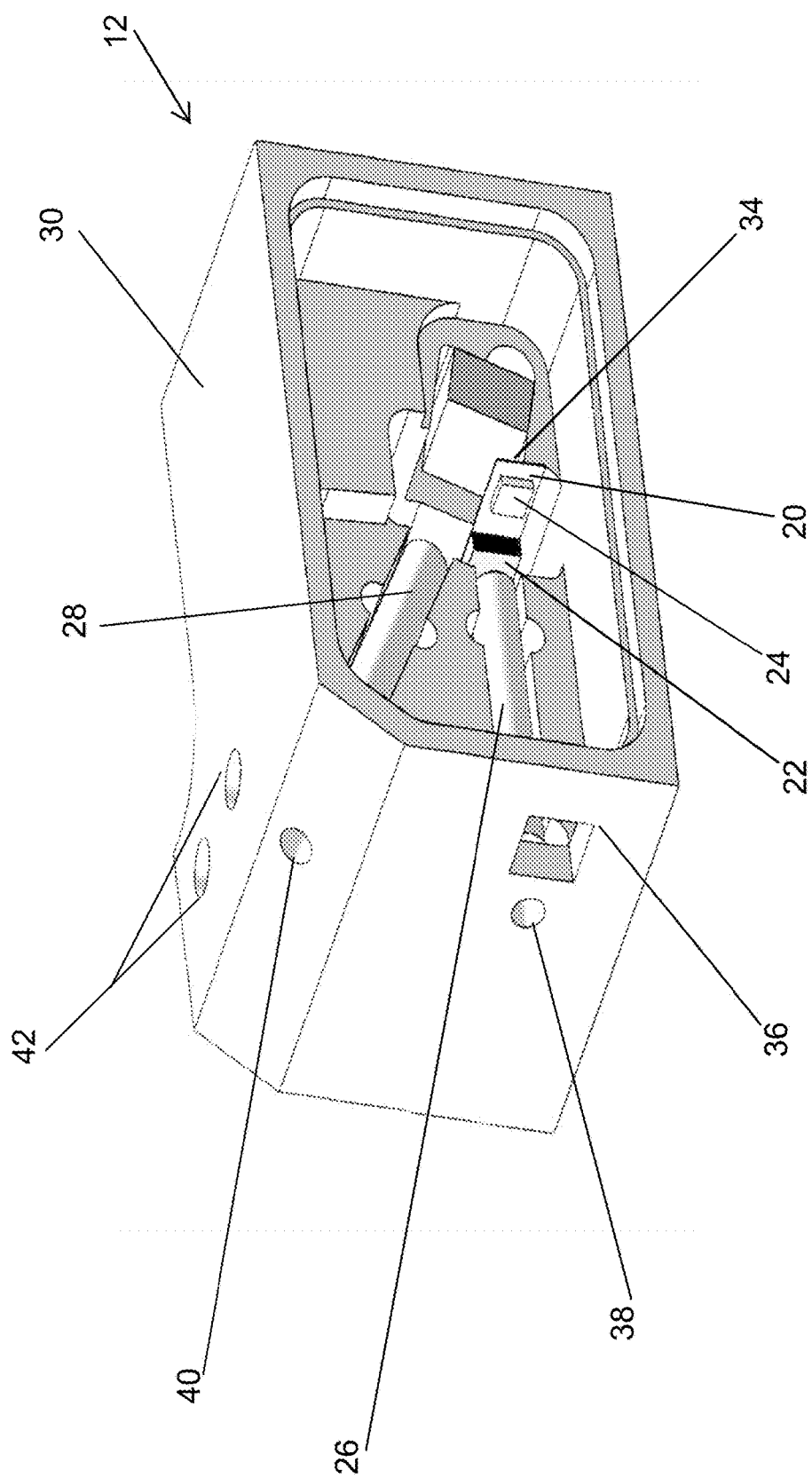
FIG. 2 is a side perspective view cross-sectional view of an exemplary apparatus for photonic pressure measurement of the present technology.

Referring now more specifically to FIGS. 1-2, photonic pressure sensor device 12 includes a cantilever 20, an etalon 22, an electromagnetic reactive material 24, a first collimator 26, and a second collimator 28 located within housing 30, although the photonic pressure sensor device 12 may include other types and/or number of elements or components in other configurations, such as additional optical components such as lenses, collimators, and mirrors, by way of example only. The present technology provides an opto-mechanical device for monitoring photonic pressure, comprising optical and mechanical components. The optical components described here comprise etalon 22 or Fabry Perot Interferometer (FPI) and collimation optics or lenses, whereas the mechanical components comprise cantilever 20 that attaches to etalon 22, and housing 30, which surrounds the device.

Cantilever 20 is pivotally attached to a fixed mount within housing 30 at a cantilever base 32 (shown in FIGS. 4A-4C), such that cantilever 20 can freely pivot with respect to fixed mount. In this example, the fixed mount is located on an inner surface of housing 30. Cantilever 20 may be formed of a number of materials known in the art. By way of example only, cantilever 20 may be formed of metals, such as aluminum, iron, and steel among others, polymer materials, such as polycarbonate, polyoxymethylene copolymers, polypropylene, poly(etheretherketone), polyvinylidenfluoride, cyclic olefin copolymers, polystyrene and SU-8 among others, ceramics materials, such as silicon nitride, carbon nanotubes, glass materials, silicon, and/or any other rigid material known in the art. It is to be understood that cantilevers can be comprised of many materials, and that the examples listed above in no way limit the scope of this technology. In one example, cantilever 20 is formed of stainless steel with a thickness of less than 1.0 mm, although other materials having other dimensions may be utilized.

Etalon 22 is coupled to cantilever 20 such that the position of etalon 22 changes based on the movement of cantilever 20. As used herein, etalon 22 or a Fabry-Perot Interferometer (FPI), refers to a coupled pair of plane parallel reflective optics in which an interference of light is generated by multiple reflections within the cavity separating the reflective surfaces. The space between the parallel reflective optics of etalon 22 may or may not be filled with material, however, the parallel reflective optics must retain optical parallelism under any axis of rotation perpendicular to the incident beam. The term etalon, Fabry-Perot Interferometer, and FPI may be used equally and interchangeably throughout this description.

Figure 4C:
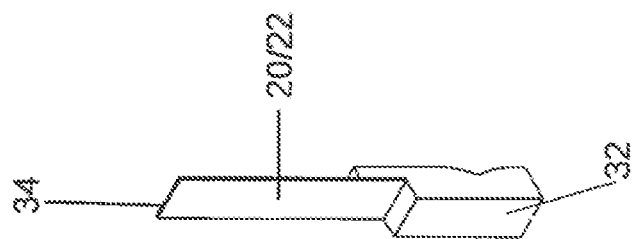
FIGS. 4A-4C are perspective views of various exemplary etalon and cantilever mounts that may be used with the present technology including: a cantilever having the etalon positioned at the distal end (free-end) relative to the cantilever mount (FIG. 4A), a cantilever with etalon positioned at a random location along the cantilever and a photon pressure zone at the distal end (free-end) of cantilever relative to the cantilever mount (FIG. 4B) and a cantilever where the cantilever comprises a hybrid cantilever-etalon held by a cantilever mount (FIG. 4C).
Figure 4B:
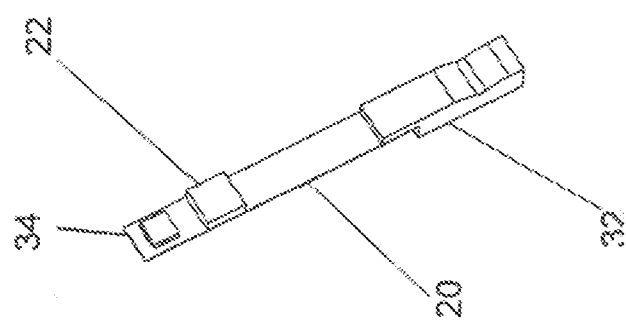
Figure 4A:
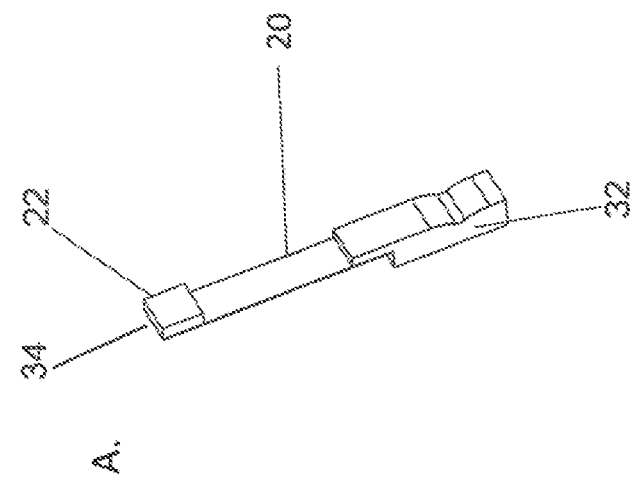
Figure 5:
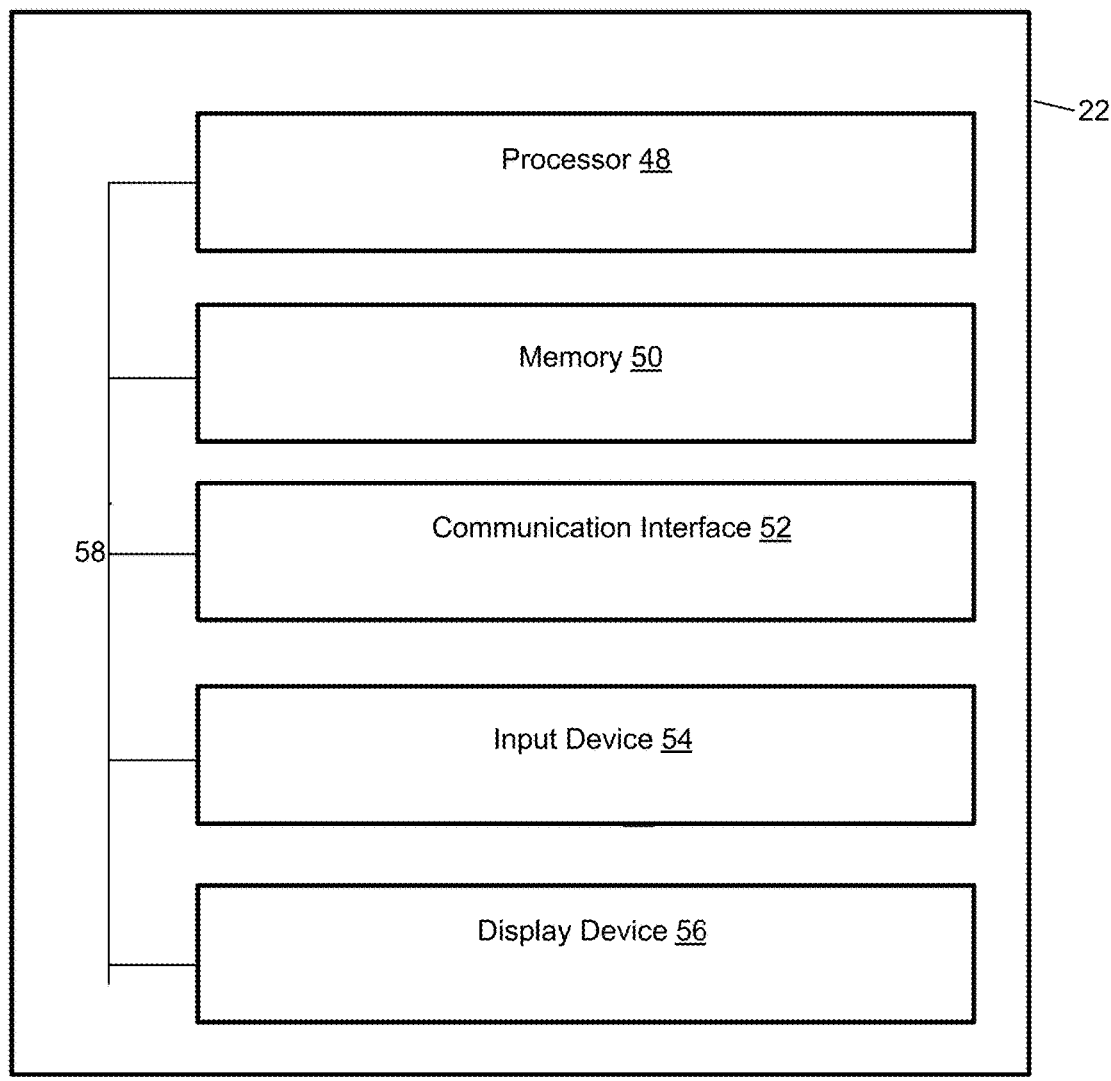
FIG. 5 is a block diagram of an exemplary analyzing computing device for use in the system illustrated in FIG. 1.

In one example, etalon 22 is coupled directly to cantilever 20 using an adhesive or epoxy, such as cationic adhesives, UV adhesives, thermoset epoxies, and two-part epoxies, by way of example only. Referring now to FIGS. 4A-4C, in one example, as shown in FIG. 4A, etalon 22 is located at a distal end 34 or free end of cantilever 20. In another example, as shown in FIG. 4B, etalon 22 is located at a point between distal end 34 and base 32 with electromagnetic reactive material 24 located proximate to distal end 34 of cantilever 20. Etalon 22 may be located anywhere along the length of cantilever 20 such that bending of cantilever 20 generates a significant optical path difference. Precise location of attachment of etalon 22 to cantilever 20 can vary by application, and is considered part of the tuning of photonic pressure sensor device 12 for specific applications. In yet another example, as shown in FIG. 4C, cantilever 20 and etalon 22 are integrated as single unit. In this example, cantilever 20 is constructed of a material that acts as etalon 22 as well as a flexing material, such that a secondary etalon is not required for operation.

Referring again to FIGS. 1 and 2, electromagnetic reactive material 24 is mounted on cantilever 20. In another example, electromagnetic reactive material 24 is a subsection of cantilever 20 itself. Electromagnetic reactive material 24 is configured to cause movement of cantilever 20 based on a photonic pressure exerted on electromagnetic reactive material 24 from an electromagnetic radiation source incident on electromagnetic reactive material 24. Attachment of the electromagnetic reactive material 24 to cantilever 20 can be achieved by any method known in the art. Non-limiting methods for attaching the electromagnetic reactive material 24 include adhesives and epoxies, deposition processes such as chemical and vapor depositions, or coating processes. Non-limiting examples of adhesives and epoxies include cationic adhesives, UV adhesives, thermoset epoxies, and two-part epoxies.

Various materials may be utilized for the electromagnetic reactive material 24 in order to either reflect or absorb electromagnetic radiation. Materials used in the electromagnetic reactive material 24 may be selected based on the type of electromagnetic radiation to be detected. By way of example, electromagnetic reactive material 24 may be selected to measure photonic pressure exerted by radio waves, microwaves, infrared (IR) light, visible light, ultraviolet (UV) light, X-rays, and/or gamma rays.

In one example, the photon pressure sensor device 12 is adapted to measure power from high power lasers, wherein the electromagnetic reactive material 24 is a material that reflects electromagnetic radiation. In this example, electromagnetic reactive material 24 may include mirrors, reflective metals, reflective plastics, or reflective glass. In another example, photon pressure sensor device 12 is adapted to measure X-ray flux, wherein the electromagnetic reactive material 24 is a material that absorbs X-ray. In this example, electromagnetic reactive material 24 may include metals and/or polymers, although any X-ray absorbing material can be utilized for electromagnetic reactive material 24. Non-limiting examples of X-ray absorbing materials include metals such as lead, tantalum and molybdenum, and non-metal materials such as polystyrene among others.

First collimator 26 is positioned within housing 30 to direct and collimate light from light source 14 to etalon 20. In this example, first collimator 26 is a 62.5 core-micrometer fiber collimator, although other types of collimators may be employed. Second collimator 28 is positioned within housing 30 to collect and collimate and interference light beam from etalon 20. In this example, second collimator 28 is positioned to collect an interference light beam that is reflected from etalon 20, although in other examples, second collimator may be positioned to collect and collimate an interference light beam that is transmitted through etalon 20, as described in further detail below. In this example, second collimator 28 is a 200-micrometer core collection collimator, although other types of collimators may be utilized.

Housing 30 is configured to provide a protective case for the photonic pressure sensor device 12 and may be formed of any suitable materials. Housing 30 is configured to house cantilever 20 and etalon 22. In one example, cantilever 20 is fixedly mounted at base 32 (as shown in FIGS. 4A-4C) at an inner surface of housing 30. In one example, housing 30 is hermetically sealed to protect the optical components located therein.

Housing 30 includes a window 36 that is positioned to receive the electromagnetic radiation to be measured. Window 36 is further positioned such that the electromagnetic radiation to be measured is incident on electromagnetic reactive material 24 to provide a photonic pressure. In one example, window 36 is formed of polystyrene, although other materials may be utilized. Housing 30 also includes an input hole 38 for receiving light from light source 14 and an output hole 40 for delivering an interference light beam from etalon 20 to detector 16. In this example, housing 30 includes mounting holes 42 on top of housing 30 for mounting photonic pressure sensor device 12 in position to receive the incident electromagnetic radiation to be measured. It is to be understood that mounting holes 42 can be present in other locations of housing 30 depending on the application.

Referring now more specifically to FIG. 1, photonic pressure measuring system 10 further includes light source 14 optically coupled to photonic pressure sensor device 12. Light source 14 may any coherent, or partially coherent, light source. By way of example only, light source 14 may include a laser, a narrow linewidth source such as an LED, or a superluminescent diode that may in addition be either spectrally or spatially filtered. In this example, light source 14 is optically coupled to a first fiber optic cable 42 that delivers light through input hole 38 to first collimator 26 to optically couple light source 14 to etalon 22.

Detector 16 is coupled to photonic pressure sensor device 12 through a second fiber optic cable 44 positioned in output hole 40 to receive an interference light beam from etalon 22 through second collimator 28. In one example, detector 16 receives an interference light beam that is reflected from etalon 22. In another example, detector 16 is positioned to receive an interference light beam transmitted through etalon 22. Detector 16 is configured to measure an intensity value for the interference light beam. In this example, detector 16 is a photodetector configured to detect an intensity value of a light beam incident on detector 16.

Analyzing computing device 18 is coupled to detector 16. Analyzing computing device 18 includes processor 48, memory 50, communication interface 52, input device 54, and display device 56, which are coupled together by bus 58 or other communication link, although other numbers and types of systems, devices, components, and elements in other configurations and locations can be used.

Processor 48 executes a program of instructions stored in memory 50 for one or more aspects of the present technology. Other numbers and types of systems, devices, components, and elements in other configurations and locations can be used to execute the program of instructions stored in memory 50.

Memory 50 stores these programmed instructions for one or more aspects of the present technology, although some or all of the programmed instructions could be stored and/or executed elsewhere. A variety of different types of memory storage devices, such as a random access memory (RAM), read only memory (ROM), hard disk, CD ROM, DVD ROM, or other computer readable medium which is read from and written to by a magnetic, optical, or other reading and writing system that is coupled to processor 38, can be used for memory 50.

Communication interface 52 is used to operatively couple and communicate between analyzing computing device 18 and one or more other computing devices via a communications network. Other types and numbers of communication networks or systems with other types and numbers of connections and configurations can be used for communication between analyzing computing device 18 and one or more other computing devices. By way of example only, the communications network could use TCP/IP over Ethernet and industry-standard protocols, including NFS, CIFS, SOAP, XML, LDAP, and SNMP. Other types and numbers of communication networks, such as a direct connection, a local area network, a wide area network, modems and phone lines, e-mail, and wireless communication technology, each having their own communications protocols, can be used by the communication networks.

The input device 54 and display device 56 of analyzing computing device 18 enable a user to interact with analyzing computing device 18, such as to input and/or view data and/or to configure, program, and/or operate analyzing computing device 18, by way of example only. Input device 54 may include a keyboard, computer mouse, and/or touch screen, and display device 56 may include a computer monitor. Other types and numbers of input devices and/or display devices could also be used in other examples.

Another aspect of the present technology relates to a method of making a photonic pressure sensor device. The method includes pivotally attaching a cantilever to a fixed mount, the cantilever having an electromagnetic reactive material located thereon that is configured to cause a movement of the cantilever based on a photonic pressure exerted on the electromagnetic reactive material from an electromagnetic radiation source incident on the electromagnetic reactive material. An etalon is coupled to the cantilever such that a position of the etalon changes based on the movement of the cantilever. A light source is optically coupled to the etalon to provide a light beam to the etalon, wherein the change in the position of the etalon causes interference of the light within the etalon resulting in an interference light beam. A light detector is positioned to receive the interference light beam from the etalon. The light detector is configured to measure an intensity value for the interference light beam.

A further aspect of the present technology relates to a method measuring photonic pressure. The method includes providing the photonic pressure sensor device of the present invention. The photonic pressure sensor device is positioned to receive electromagnetic radiation from the electromagnetic radiation source incident on the electromagnetic reactive material. The light beam is provided to the etalon. The interference light beam is collected with the detector. The intensity value of the interference light beam is measured. The photonic pressure exerted on the electromagnetic reactive material is determined based on the measured intensity value for the interference light beam.

An exemplary operation of photonic pressure measuring system 10 including photonic pressure sensor device 12 will now be described with respect to FIGS. 1-4.

First, photonic pressure sensor device 12 is positioned to receive electromagnetic radiation from the electromagnetic radiation source for measurement. Photonic pressure sensor device 12 may be utilized to measure photonic pressure exerted by radio waves, microwaves, infrared (IR) light, visible light, ultraviolet (UV) light, X-rays, and/or gamma rays, by way of example only. Photonic pressure sensor device 12 is positioned such that the electromagnetic radiation to be measured passes through window 36 as is incident on electromagnetic reactive material 24, such that the electromagnetic radiation exerts a photonic pressure on cantilever 20.

The physical origin of radiation pressure arising from momentum of light appears as a fundamental result in major theories of modern physics. In electromagnetism, as described in Mansuripur, M., "Radiation Pressure and the Linear Momentum of the electromagnetic Field," Optics Express, 12(22), pp. 5375-5401, (2004), the disclosure of which is incorporated herein by reference, photon momentum arises as a result of the energy flux density of an electromagnetic field given by the Poynting vector:

$$S = E \times H \tag{1}$$

as described in Li et al., "NIST MEASUREMENT SERVICES: High Power Laser Calibrations at NIST,", NIST Special Publication 250-77 (2008) and Cromer, et al., "Absolute High-Power Laser Measurements with a Flowing Water Power Meter," 11th Conference on New Developments and Applications in Optical Radiometry, Maui, Hi., USA. (Sep. 19-23, 2011), the disclosures of which are incorporated by reference, where E is the electric field, and H is the magnetic field.

For the simple case of a plane electromagnetic wave, a calculation of time averaging and integration of the flux reduces to following equation:

$$\int \langle S \rangle dA/c = E/c = p \qquad (2)$$

where the energy E can be interpreted as due to a photon, and c is the speed of light.

In special relativity as described in Mansuripur, M., "Radiation Pressure and the Linear Momentum of the electromagnetic Field," Optics Express, 12(22), pp. 5375-5401, (2004), the disclosure of which is incorporated herein by reference, the energy of a particle is given as $E^2=p^2c^2+mc^4$, so that a massless particle such as the photon (m=0) has an associated momentum (p) given by the equation:

$$p = E/c \qquad (3)$$

In the elementary formulations of quantum mechanics and wave-particle duality involving Planck's constant (h), the quantization of photon energy, (E=hv) combined with the Heisenberg uncertainty principle (p=h/λ), and the intrinsic relation between wavelength (λ) and frequency (v), c=λv, also gives momentum (p) as set forth in equation (3) above.

In optical terminology, it is straightforward to work with the Irradiance I (energy flux density) in Watts/m² so that the radiation pressure P=I/c (for an absorbing material at normal incidence) has convenient SI dimensional units of N/m². For a perfectly reflecting material, as a result of Newton's third law of motion, the radiation pressure or force (P) of a beam of light is given as:

$$P = 2I/c \qquad (4)$$

The basic conversion factor of an approximate 1 W/m² results in a radiation pressure of 3.3e-09 N/m². Exact expressions can also be derived and available for cases of partial reflectance of an optical component at non-normal incidence as described in Pozar, T., "Oblique Reflection of a Laser Pulse From a Perfect Elastic Mirror," Optics Letters, 39(1), (2014), the disclosure of which is incorporated by reference. For example, the radiation force (P), due to photon momentum from an X-ray source at an arbitrary angle of incidence θ to the normal is given as:

$$P = 2I/c[R + (1-R)\kappa/2]\cos(\theta) \qquad (5)$$

where R is the mirror reflectance, and κ is the absorbance of the optical component. The associated force (F) of the beam is simply the integral over the area of the beam as described in Pozar, T., "Oblique Reflection of a Laser Pulse From a Perfect Elastic Mirror," Optics Letters, 39(1), (2014) and Wu et al., "Measurement of Photon Pressure," XVIII Imeko World Congress, Metrology for a Sustainable Development (2006), the disclosures of which are incorporated by reference, as given by the following equation:

$$F = \int P dA \qquad (6)$$

The present technology uses etalon 22 coupled to cantilever 20 to measure the force (F) due to photon pressure. An oncoming beam of electromagnetic radiation from a photon source incident on the any portion of cantilever 20 transfers a reactive impulse due to Newton's third law. Thus, electromagnetic radiation passes through window 36 into housing 30 of photon pressure sensor device 12, landing incident on electromagnetic reactive material 24 of cantilever 20. Contact of electromagnetic reactive material 24 by electromagnetic radiation causes photonic pressure, which causes deflection of cantilever 20.

Deflection of cantilever 20 as a result of the photonic pressure also results in concomitant movement of etalon 22. Cantilever 20 is designed specifically to bend so that the attached etalon 22 rotates. If the beam effecting bending of cantilever 20 by photon pressure is coherent, or partially coherent, then in one example, etalon 22 can be placed on the cantilever such that a portion of the beam for which photonic pressure is being measured is also incident on etalon 22. If the beam effecting bending of cantilever 20 is not coherent, then another example can have etalon 22 placed on cantilever 20 such that a separate coherent beam, such as a probe laser beam from light source 14, can be aimed such that it is incident on etalon 22.

In this example, movement of etalon 22 is measured using a light beam from light source 14 as described in further detail below. Referring more specifically to FIG. 3, light source 14 provides a first light beam 46 that is delivered to etalon 22. In this example, first light beam 46 is a coherent, or partially coherent, light beam. As described above, light source 14 delivers first light beam 46 to photon pressure sensor device 12 through first fiber optic cable 42. First light beam 46 is directed through first collimator 26 and provided to etalon 22.

The change in the position of etalon 22 as a result of the photonic pressure and concomitant movement of cantilever 20 causes interference of collimated first light beam 46 within etalon 22. The interference produces an interference light beam 48A reflected from etalon 22 and an interference light beam 48B that is transmitted through etalon 22. Movement of etalon 22 changes the optical path difference (OPD) causing changes to the intensity of interference light beam 48A.

Next, interference light beam 48A or 48B is collected and directed to detector 16. In this example, interference light beam 48A is collected by second collimator 28 and provided to detector 16, such as a photodetector, through second fiber optic cable 44, although other examples may involve collecting interference light beam 48B.

Detector 16 measures an intensity value of interference light beam 48A. Detector provides a signal to analyzing computing device 18 representative of the intensity value of interference light beam 48A.

Analyzing computing device 18 receive the measured intensity value for, in this example, interference light beam 48A from detector 18 and determines the photonic pressure exerted by the electromagnetic radiation to be measured on electromagnetic reactive material 24 based on the measured intensity value for interference light beam 48A. Cantilever 20 is designed specifically to bend so that the attached etalon 22 rotates. As cantilever 20 bends and rotational motion of etalon 22 is initiated, interference light beam 48A experiences an Optical Path Difference (OPD) within the cavity of etalon 22. The end result is a pure opto-mechanical transduction of the radiation force to a detectable modulated analog signal.

The optical response of the present technology is generated by the change in OPD due to rotation of etalon 22 representing a displacement due to photon pressure based acceleration. This acceleration is applied to flexible cantilever 20.

In one example, the mechanical motion of cantilever 20 is modeled assuming cantilever 20 conforms to simple Euler-Bernoulli beam theory with quasi-static approximations based on taking into account deformational stress due to bending moment force. Here, cantilever 20 is assumed to be uniformly loaded with stationary base 32 fixedly mounted on an inner surface of housing 30, with no end mass allowing calculation of the z-deflection at the linear extent of etalon 22 (x=L).

The fundamental assumptions of Euler-Bernoulli theory as described in Kleppner, et al., *An Introduction to Mechanics*, Cambridge University Press (2010), the disclosure of which is hereby incorporated by reference, are that deflections due to deformation are small, independent of z, and cross-sections are orthogonal along the body axis (x). Note that the Euler-Bernoulli model ignores transverse shear forces. A straightforward analysis yields the following equation, as described in Kleppner, et al., *An Introduction to Mechanics*, Cambridge University Press (2010) and Spiegel, M., *Theoretical Mechanics*, Schaum Publishing, New York (1968), the disclosures of which are hereby incorporated by reference:

$$z(L) = F \frac{L^3}{3EI} \quad (7)$$

where F is the applied moment force, E is Young's modulus for the material that makes up cantilever 22, L is the length of cantilever 20, I is the area moment of inertia about the neutral body rotation axis (y), and t is the thickness of cantilever 20.

The Euler-Bernoulli theory ignores transverse shear and strain effects on deformation and therefore significantly underestimates the beam deflection for large applied moments (g-forces). The more general theory of Timoshenko as described in Stephen, "The Second Spectrum of Timoshenko Beam Theory," Journal of Sound and Vibration, 292:372-89 (2006), the disclosure of which is incorporated herein by reference considers these effects and rotational inertia in cantilever beam equations.

The solution of the Euler-Bernoulli beam equation as described in Spiegel, M., *Theoretical Mechanics*, Schaum Publishing, New York (1968), the disclosure of which is hereby incorporated by reference, given boundary conditions for a beam that is fixed on one end and free on the other end, can be used to determine the natural (resonant) frequencies of cantilever 20. The analysis yields a solution of the beam transverse displacement z(x) as a function of lengthwise beam coordinate (x) of the form:

$$z(x)=A[\cos(\eta x)+\cosh(\eta x)]+B[\cos(\eta x)-\cosh(\eta x)]+C[\sin(\eta x)+\sin h(\eta x)]+D[\sin(\eta x)-\sin h(\eta x)] \quad (8)$$

where the modal parameter λ is:

$$\eta = (\mu \omega^2 / EI)^{1/4} \quad (9)$$

with μ being the mass per unit length (or uniform density times cross-sectional area), ω is the frequency, E is Young's modulus of the material of cantilever 20, and I is the rotational moment of inertia. Non-trivial modal solutions exist only when the modal parameter satisfies the following equation:

$$\cos(\lambda_n L)\cos h(\lambda_n L)+1=0 \quad (10)$$

The first two solutions occur for values of the modal parameter such that $\lambda_1 *L=1.875$ and $\lambda_2 *L=4.694$. The natural resonant frequencies of cantilever 20 for a given mode can then be deduced ($\omega$n). The basic Euler-Bernoulli Framework described above applies to deflection based on a static force and the determination of maximum frequency response for the first two modes of vibration, but can be extended to higher order modes.

The present technology is based on angular rotation and centripetal acceleration of etalon 22 inducing a phase change of light within etalon 22 that acts as an interferometer due to a change in Optical Path Difference (OPD), which is a function of angle. When the device experiences a vector acceleration A=(a,b,c) due to force F from a photonic pressure, the component acceleration along one linear direction, for example the x-direction without loss of generality, etalon 22 will rotate about its optical axis placed parallel to the x-axis (i.e. plane surface in the y-z plane). In a simplified example, as etalon 22 experiences rotation about a pivot, it will experience a torque T=r×F, where r is the moment to the center of mass of etalon 22. This torque will initiate rotation of etalon 22 as described in Spiegel, M., *Theoretical Mechanics*, Schaum Publishing, New York (1968), the disclosure of which is hereby incorporated by reference:

$$T=I\alpha, \alpha=d^2\theta/dt^2 \quad (11)$$

where α is the angular acceleration or 2nd derivative of the rotation angle, and I is the moment of inertia of etalon 22 about the pivot point that is the origin of the coordinate system. After a time t (assume zero initial displacement and velocity for simplicity) the angle subtended due to accelerating motion is given by the following equation:

$$\theta(t) = \frac{\tau}{2I} t^2 \quad (12)$$

Any change in the angle of rotation will cause a change in OPD of light interfering within etalon 22:

$$OPD=2\pi n(T)L \cos(\theta)/\lambda \quad (13)$$

Here L is the width of the spacer cavity, n is the refractive index of the spacer material and denoted as varying with temperature, θ is the angle of incidence, and λ is the wavelength of light. The optical interference intensity of both transmitted and reflected light from etalon 22 will be modulated due to interference within etalon 22 and the change in OPD. Light from either the transmitted or reflected beam from etalon 22 can be measured, and it is sufficient for the purposes of this invention to consider measuring either the transmitted or reflected light. In transmission, the observed intensity (on a photodetector) is given by the following equation as described in Born, et al., *Principles of Optics*, 7th Edition, Cambridge University Press, (1999), the disclosure of which is hereby incorporated by reference:

$$I(\theta(t)) = \frac{I_0}{1 \to F\sin^2(OPD)}, F = \frac{4R_c}{(1-R_c)^2} \quad (14)$$

where F is the coefficient of Finesse, and $R_c$ is the reflectance of the coating layers on each side of etalon 22, and $I_o$ is the input X-ray flux.

A rotation will shift the optical response profile and modulation of the optical signal will occur due to the convolution of the coherent optical light with a resonant spectral peak of etalon 22 characterized by a FWHM and Free Spectral Range (FSR) as described in Born, et al., *Principles of Optics*, 7th Edition, Cambridge University Press, (1999), the disclosure of which is hereby incorporated by reference. By observing the modulated intensity of light from detector 16, with fast data acquisition to capture phase cycles (at least an order of magnitude above the Nyquist level), the precise value of rotation may be directly determined by analyzing computing device 18. The angular acceleration and torque may be then calculated from which the acceleration can be computed using the mechanical moment r of etalon 22, by way of example only:

$$a = r\alpha \quad (15)$$

The present technology is particularly sensitive and responsive to transient and fluctuation events that are of interest to precise and fast flux monitoring and data acquisition in high power laser and X-ray measurements. Also, since photon pressure measuring system 10 uses a pure optical signal for detection, the noise characteristic is independent of any mechanical motion of etalon 22. The noise floor is simply limited by detector 16, dark current, and optical shot noise. With state-of-the-art trans-impedance amplifiers, noise equivalent power (NEP) in the low picowatt range can be attained.

The present technology is sensitive to rotation (at thresholds of an arc second or less), so that even a tiny change in OPD, of a few arc seconds of rotation, will shift the optical response and a full modulation of the optical signal will occur within an equivalent shift of spectral separation between the peaks (FSR). Measured sensitivity of less than 1 µG is demonstrated given even low sampling rates of only five kilohertz per degree of rotation. The temperature sensitivity is well characterized and deterministically dependent on the refractive index and coefficient of thermal expansion of the optical component.

As should be obvious to one skilled in the art, the embodiments described above can be adapted to measure or monitor other types of electromagnetic radiation. Thus, the above descriptions in no way limit the general principles described here within, but instead describe exemplary and non-limiting embodiments of the present invention.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A photonic pressure sensor device comprising:
   a cantilever pivotally attached to a fixed mount, the cantilever having an electromagnetic reactive material located thereon, wherein the electromagnetic reactive material is configured to cause a movement of the cantilever based on a photonic pressure exerted on the electromagnetic reactive material from an electromagnetic radiation source incident on the electromagnetic reactive material;
   an etalon coupled to the cantilever such that a position of the etalon changes based on the movement of the cantilever;
   a light source optically coupled to the etalon to provide a light beam to the etalon, wherein the change in the position of the etalon causes interference of the light beam within the etalon resulting in an interference light beam; and
   a light detector positioned to receive the interference light beam from the etalon and configured to measure an intensity value for the interference light beam.

2. The photonic pressure sensor device of claim 1 further comprising:
   a housing configured to house the cantilever and the etalon with the cantilever attached to the fixed mount at an inner surface of the housing, the housing having a window positioned to permit electromagnetic radiation from the electromagnetic radiation source to enter the housing such that the electromagnetic radiation is incident on the electromagnetic reactive material.

3. The photonic pressure sensor device of claim 2, wherein the housing is hermetically sealed.

4. The photonic pressure sensor device of claim 1, wherein the light detector is positioned to receive the interference light beam transmitted or reflected from the etalon.

5. The photonic pressure sensor device of claim 1 further comprising:
   a first fiber optic cable optically coupled to the light source and positioned to transmit the light beam to the etalon; and
   a second fiber optic cable optically coupled to the light detector and positioned to collect the interference light beam from the etalon to deliver the interference light beam to the light detector.

6. The photonic pressure sensor device of claim 1, wherein the cantilever comprises a base pivotally attached to the fixed mount and a distal end located opposite the base, wherein the electromagnetic reactive material is positioned proximate the distal end of the cantilever.

7. The photonic pressure sensor device of claim 1, wherein the electromagnetic reactive material is a material that absorbs or reflects electromagnetic radiation.

8. The photonic pressure sensor device of claim 1 further comprising:
   an analyzing computing device coupled to the light detector, the analyzing computing device comprising a processor and a memory coupled to the processor which is configured to execute one or more programmed instructions comprising and stored in the memory to:
   receive the measured intensity value for the interference light beam from the light detector; and
   determine the photonic pressure exerted on the electromagnetic reactive material based on the measured intensity value for the interference light beam.

9. The photonic pressure sensor device of claim 1, wherein the etalon is integral to the cantilever.

10. The photonic pressure sensor device of claim 1, wherein the cantilever is constructed of stainless steel having a thickness of less than 1.0 mm.

11. A method of measuring photonic pressure comprising:
    providing the photonic pressure sensor device of claim 1;
    positioning the photonic pressure sensor device to receive electromagnetic radiation from the electromagnetic radiation source incident on the electromagnetic reactive material;
    providing the light beam to the etalon;
    collecting the interference light beam with the detector;
    measuring the intensity value of the interference light beam; and determining the photonic pressure exerted on the electromagnetic reactive material based on the measured intensity value for the interference light beam.

12. The method of claim 11 further comprising:
positioning the light detector to receive the interference light beam reflected or transmitted from the etalon.

13. The method of claim 11 further comprising:
providing a first fiber optic cable optically coupled to the light source and positioned to transmit the light beam to the etalon; and
providing a second fiber optic cable optically coupled to the light detector and positioned to collect the interference light beam from the etalon to deliver the interference light beam to the light detector.

14. The method of claim 11 further comprising:
providing an analyzing computing device coupled to the light detector, the analyzing computing device comprising a processor and a memory coupled to the processor which is configured to execute one or more programmed instructions comprising and stored in the memory to:
receive the measured intensity value for the interference light beam from the light detector; and
determine the photonic pressure exerted on the electromagnetic reactive material based on the measured intensity value for the interference light beam.

15. A method of making a photonic pressure sensor device comprising:
pivotally attaching a cantilever to a fixed mount, the cantilever having an electromagnetic reactive material located thereon, wherein the electromagnetic reactive material is configured to cause a movement of the cantilever based on a photonic pressure exerted on the electromagnetic reactive material from an electromagnetic radiation source incident on the electromagnetic reactive material;
coupling an etalon to the cantilever such that a position of the etalon changes based on the movement of the cantilever;
optically coupling a light source to the etalon to provide a light beam to the etalon, wherein the change in the position of the etalon causes interference of the light within the etalon resulting in an interference light beam; and
positioning a light detector to receive the interference light beam from the etalon, wherein the light detector is configured to measure an intensity value for the interference light beam.

16. The method of claim 15 further comprising:
providing a housing configured to house the cantilever and the etalon with the cantilever attached to the fixed mount at an inner surface of the housing, the housing having a window positioned to permit electromagnetic radiation to enter the housing such that the electromagnetic radiation is incident on the electromagnetic reactive material.

17. The method of claim 16, wherein the housing is hermetically sealed.

18. The method of claim 15, wherein the light detector is positioned to receive the interference light beam reflected or transmitted from the etalon.

19. The method of claim 15 further comprising:
optically coupling a first fiber optic cable to the light source, the first fiber optic cable positioned to transmit the light beam to the etalon; and
optically coupling a second fiber optic cable optically coupled to the light detector, the second fiber optic cable positioned to collect the interference light beam from the etalon to deliver the interference light beam to the light detector.

20. The method of claim 15, wherein the cantilever comprises a base pivotally attached to the fixed mount and a distal end located opposite the base, wherein the electromagnetic reactive material is positioned proximate the distal end of the cantilever.

21. The method of claim 15, wherein the electromagnetic reactive material is a material that absorbs or reflects electromagnetic radiation.

22. The method of claim 15 further comprising:
coupling an analyzing computing device to the light detector, the analyzing computing device comprising a processor and a memory coupled to the processor which is configured to execute one or more programmed instructions comprising and stored in the memory to:
receive the measured intensity value for the interference light beam from the light detector; and
determine the photonic pressure exerted on the electromagnetic reactive material based on the measured intensity value for the interference light beam.

23. The method of claim 15, wherein the etalon is integral to the cantilever.

24. The method of claim 15, wherein the cantilever is constructed of stainless steel having a thickness of less than 1.0 mm.

* * * * *